United States Patent [19]
Tóth et al.

[11] 3,964,894
[45] June 22, 1976

[54] METHOD OF CONTROLLING PLANT GROWTH

[75] Inventors: Géza Tóth; Gábor Szabó; György Eibel; Éva Somfai, all of Budapest, Hungary

[73] Assignee: Chinoin Gyógyszer-és Vegyészeti Termekek Gyára RT, Budapest, Hungary

[22] Filed: Apr. 8, 1974

[21] Appl. No.: 458,999

Related U.S. Application Data

[63] Continuation-in-part of Ser. No. 168,443, Aug. 2, 1971, abandoned.

[30] Foreign Application Priority Data
July 31, 1970 Hungary.............................. CI 1017

[52] U.S. Cl......................................... 71/90; 71/96; 71/77; 47/57.6; 260/326.13 A
[51] Int. Cl.²........................................... A01N 9/22
[58] Field of Search...................... 71/77, 80, 90, 96

[56] References Cited
UNITED STATES PATENTS

| | | | |
|---|---|---|---|
| 2,204,213 | 6/1940 | Grace | 71/77 |
| 3,051,723 | 8/1962 | Fritz | 71/96 |
| 3,420,838 | 1/1969 | Szmuszkovicz | 71/96 |

OTHER PUBLICATIONS
Toth et al., Chem. Abst. vol. 77 (1972) 5329p.

*Primary Examiner*—Lewis Gotts
*Assistant Examiner*—Catherine L. Mills
*Attorney, Agent, or Firm*—Karl F. Ross; Herbert Dubno

[57] ABSTRACT

A method of controlling plant growth wherein the plant or its seed are treated with thiazolyl-indolyl compounds.

6 Claims, No Drawings

METHOD OF CONTROLLING PLANT GROWTH

This application is a continuation-in-part of application Ser. No. 168,443, filed Aug. 2, 1971 now abandoned.

The present invention relates to a method of controlling plant growth using compounds described in the aboveidentified application.

The present invention deals, more particularly, with compounds of the formula

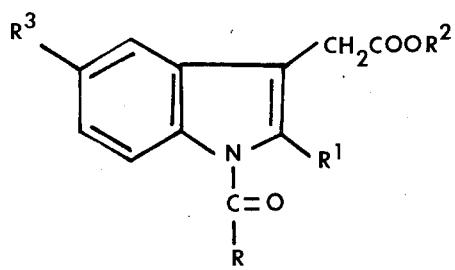

(I)

in which R is 2-furyl-, 5-nitro-2-furyl-, 2-bromothiazol-4-yl and 2-chlorothiazol-4-yl;
$R^1$ is methyl;
$R^2$ is hydrogen; and
$R^3$ is methoxy.
These compounds thus have the formula

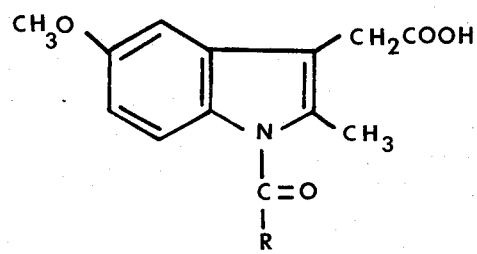

(IA)

These compounds can be obtained by:
a. reacting compounds of the formula

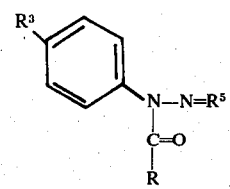

(II)

(where R and $R^3$ have the aforedescribed meanings while $R^5$ represents two hydrogen atoms or an alkylidene group) produced by the direct acylation of hydrazines or hydrazones obtained from aryl hydrazines and their derivatives, respectively, by their treatment with oxocompounds, with compounds of the formula

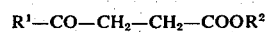

(III)

(where $R^1$ and $R^2$ have the abovedescribed meaning), and, if desired, setting free the free acid from the obtained product, or b. subjecting to cyclization, compounds of the formula

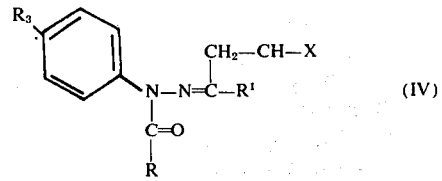

(IV)

where X represents a —CHO, —CH$_2$OH, —CH$_2$OR$^7$, —CN, —COOH or —CH——(OR$^7$)$_2$ group and $R^7$ represents an alkyl group) or c. reacting compounds of the formula

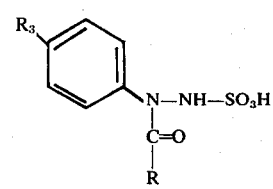

with a compound of formula III (where $R^1$ and $R^2$ have the abovespecified meaning),
and converting, when desired, the formed compound into a salt or setting it free from its salts.

The compounds produced according to the present invention have, aside from the properties described for these compounds in the above-identified application, surprising plant-growth promoting effect when applied at low concentrations to the growth site or when used to treat seeds of a plant.

A preferred method of producing the compounds is variant a) which, because of its simple nature and economic mode of realization, offers the advantage of affording intermediates which are readily isolatable, directly utilizable in the synthesis of indole and possessing also alone useful therapeutic properties.

In the process evolved for the production of $N^1$-acyl-$N^2$-arylhydrazines, the isopropylidene group obtainable from acetone and possessing special properties can be chosen for the protection of the $N^2$ atom.

This offers the following advantages: $N^2$-iso-propylidene aryl hydrazine can be produced simply and readily on industrial scale without any isolation of the labile and hardly processable intermediates; it makes possible selective $N^1$-acylation under simple conditions; it is suitable by itself for the synthesis of indole; it can be exchanged readily for other oxocompounds suitable for the synthesis of indole, and it is also directly applicable in the synthesis of indole.

Subsequent to $N^1$-acylation it can be converted into $N^1$-(acyl)-$N^1$-(aryl)-hydrazine or into its hydrochloride without any detrimental effect to the $N^1$-acyl group, by removing the isopropylidene group in a simple way.

The ring closure of $N^1$-substituted phenylhydrazones can be carried out under moderate conditions even at room temperature, and this leads to a marked yield increase.

Most aryl hydrazines, e.g. including methoxy-phenylhydrazine are rather unstable compounds. Thus, the desired intermediates can be obtained only under difficult conditions, by isolation of the phenylhydrazines and by the formation of hydrazones from the isolated products. We have found, however, that on hydrolyzing sodium-p-methoxy-phenylhydrazine-sulphonate in a water-hydrochloric acid-ethanol system, and neutralizing the reaction mixture with a solution of sodium carbonate, the hydrazone can be obtained in a crystalline form from the aqueous-ethanolic solution by adding acetone, the preferred oxo-compound. On dissolving the hydrazone obtained in this way in an appropriate solvent, $N^1$-acylation can be carried out directly after the dehydration of the solution.

The acetone-$N^1$-acyl-$N^1$-arylhydrazone obtained by working up the reaction mixture can also be directly used for the synthesis of the indole.

Another advantage offered by the process of the invention is that on adding, after acylation, aqueous hydrochloric acid to the reaction mixture, the isopropylidene group can be removed, and by applying a polar solvent, $N^1$-acyl-$N^1$-arylhydrazine hydrochloride can be obtained.

The desired derivative of N-acyl-indole-3-acetic acid derivative can be prepared directly from the obtained $N^1$-acyl-$N^1$-arylhydrazine hydrochloride or the $N^1$-acyl-$N^1$-arylhydrazine liberated from the hydrochloride can be converted into the desired derivatives of N-acyl-indole-3-acetic acid.

Preferably the compounds of the present invention are dissolved in water and, at a concentration of $10^{-3}$ to $10^{-20}$%, are used to treat seeds by soaking or spraying the latter. The seedlings manifest a surprising increase in foliage and root growth (measured by weight) over that of control plants from untreated seeds. When solutions of the indicated concentrations are applied to agricultural plots in which seed has been sown a similar percocious development of the seedlings is noted.

The preferred compounds are:
1-(5-nitro-2-furoyl)-2-methyl-5-methoxy-indole-3-yl-acetic acid;
1-(2-furoyl)-2-methyl-5-methoxy-indole-3-yl-acetic acid;
1-(2-bromo-thiazol-4-yl-carbonyl)-2-methyl-5-methoxy-indole-3-yl-acetic acid;
1-(2-chloro-thiazol-4-yl-carbonyl)-2-methyl-5-methoxy-indole-3-yl-acetic acid.

EXAMPLE 1

80 g of acetone-(p-methoxyphenyl)-hydrazone as obtained moist on the suction are dissolved in 700ml of a 1:1 mixture of benzene and toluene, dried on sodium sulphate, filtered and the filtrate washed with 50 ml of benzene. On cooling the solution to 0°C and adding 40 ml of pyridine, 87.5 ml. (0.5 mole) of 5-nitro-2-furancarboxylic acid chloride are dropwise added at 0°–5°C. After stirring for 30 minutes the precipitated pyridine hydrochloride is filtered off, the residual solution washed with water and shaken with 160 ml of 6 N hydrochloric acid. The precipitated substance is filtered by suction, washed with benzene, taken up with water and neutralized with sodium carbonate. The precipitated $N^1$-(5-nitro-2-furoyl)-$N^1$-(p-methoxyphenyl)-hydrazine is filtered by suction and washed with water. Yield: 67.5 g, m.p. 163°–164°C.

45.1 g (0.162g-mole) of $N^1$-(5-nitro-2-furoyl)-$N^1$-(p-methoxyphenyl)-hydrazine are mixed with 160 ml of acetic acid, 27.8 ml of levulinic acid and 2.8 ml of concentrated sulphuric acid and the mixture kept at 80°–85°C for 1.5 hour. On cooling, the mixture is cooled with 158 ml of water, and the formed 1-(5-nitro-2-furoyl)-2-methyl-5-methoxy-indole-3-yl acetic acid recrystallized from ethanol. Yield: 35.8 g, m.p. 183°–184°C, 62% referred to $N^1$-(5-nitro-2-furoyl)-$N^1$-(p-methoxyphenyl)-hydrazine.

EXAMPLE 2

30 g of acetone-(p-methoxyphenyl)-hydrazone as obtained moist on the suction filter are dissolved in 300 ml of benzene, dried on sodium sulphate, filtered and the filtrate washed with 30 ml of benzene. On cooling the solution to 5°C, 8 ml of α-picoline are added, and a solution of 24.8 g (0.08 g-mole) of 2-bromo-thiazole-4-carboxylic acid chloride poured to the mixture at 0°–5°C. On stirring the reaction mixture for 2 hours, it is filtered, washed with water and shaken with 120 ml of a 1:1 mixture of hydrochloric acid and water. The aqueous phase is separated while the solvent phase evaporated almost to dryness in vacuum. On cooling, the precipitated $N^1$-(2-bromo-thiazol-4-yl-carbonyl)-$N^1$-(p-methoxyphenyl)-hydrazine hydrochloride is filtered by suction, washed with some benzene, dried in air, taken up with water and neutralized with sodium carbonate. Yield: 12.6 g, m.p. 125°–126°C.

A solution of 12.6 g of $N^1$-(2-bromo-thiazol-4-yl-carbonyl)-$N^1$-(p-methoxyphenyl)-hydrazine, prepared as specified above, in 50 ml of acetic acid is mixed with 14 ml of levulinic acid and 2.4 ml of concentrated sulphuric acid, then the mixture heated for 2 hours at 80°–85°C. After cooling, the reaction mixture is diluted with 50 ml of water, the precipitated 1-(2-bromo-thiazol-4-yl-carbonyl)-2-methyl-5-methoxy-indole-3-yl acetic acid filtered and recrystallized from ethanol. Yield: 8.18 g (13.7%), m.p. 169°–171°C.

EXAMPLE 3

21.5 g of acetone-(p-methoxyphenyl)-hydrazone as obtained moist on the suction filter are dissolved in 150 ml of benzene, dried on sodium sulphate, then treated with 4 ml of α-picoline and a solution of 12 g (0.045-mole) of 2-clorothiazole-4-carboxylic acid chloride in 80 ml of benzene at 5°C. After stirring for 2 hours the reaction mixture is filtered, washed with water and shaken with 50 ml of a 1:1 mixture of hydrochloric acid and water. The precipitated substance is filtered by suction, dissolved in water and neutralized with sodium carbonate. The precipitated $N^1$-(2-chlorothiazole-4-yl-carbonyl)-$N^1$-(p-methoxyphenyl)-hydrazine (5.8 g., m.p. 126°C) is heated in 16 ml of acetic acid for 2 hours at 80°–85°C after addition of 6 ml of levulinic acid and 0.7 ml of concentrated sulphuric acid. On dilution with water, the precipitated substance is recrystallized from ethanol, affording 5.22 g. (19.4%) of 1-( 2-chlorothiazole-4-yl-carbonyl)-2-methyl-5-methoxy-indole-3-yl-acetic acid, m.p. 158°–160°C.

EXAMPLE 4

To a suspension of 128 g. (0.5 g-mole) of sodium p-methoxyphenyl-hydrazine-sulphonate monohydrate in 500 ml of methanol, 94 ml of concentrated hydrochloric acid is poured in about 10 minutes under stirring at 60°–65°C to the mixture. After another 10 minutes stirring, the mixture is cooled to room temperature and neutralized with 318 g. of a 20% solution of sodium carbonate. On pouring 87 ml of acetone to the obtained aqueous solution, the formed crystalline acetone-(p-methoxyphenyl)-hydrazone is filtered by suction after allowing the mixture to stand for 30 minutes, washed with a 1:1 mixture of methanol and water, and with water. (On drying in vacuum, 80 g of acetone-(p-methoxyphenyl)-hydrazone, m.p. 95°–98°C under decomposition, are obtained in 90% yield).

The obtained product serves as starting material in Examples 1 to 3 in a moist state as obtained on the suction filter.

EXAMPLE 5

About 100 g of acetone-(p-methoxyphenyl)-hydrazone as obtained moist on the suction filter from 128 g. (0.5 g-mole) of sodium p-methoxyphenyl-hydrazine-sulphonate monohydrate are dissolved in 700 ml of a 1:1 mixture of benzene and toluene, dried on sodium sulphate, filtered and the filtrate washed with 50 ml of benzene. The solution is cooled to 0°C, 40 ml of pyridine are added, and 87.5 ml. (0.5 g-mole) of 5-nitro-2-furancarboxylic acid chloride are dropwise. After stirring for 30 minutes, the solvent phase is washed with 400 ml of water, dried on sodium sulphate and evaporated in vacuum. Acetone-$N^1$-(5-nitro-2-furoyl)-$N^1$-(methoxyphenyl)-hydrazone obtained as an oily residue is dissolved in 300 ml of acetic acid, 40 ml of levulinic acid and thereafter 15.5 ml of concentrated sulphuric acid added, and the mixture heated for an hour at 80°–85°C. On cooling, the mixture is diluted with water, and the precipitated 1-(5-nitro-2-furoyl)-2-methyl-5-methoxy-indole-3-yl acetic acid recrystallized from ethanol. Yield: 43 g. (24%, referred to sodium p-methoxy-phenyl-hydrazine-sulphonate monohydrate), m.p. 179°C.

EXAMPLE 6

To a solution of 27.7 g. (0.1 g-mole) of $N^1$-(5-nitro-2-furoyl)-$N^1$-(p-methoxyphenyl)-hydrazine in 150 ml of acetic acid, 20 ml of levulinic acid are added. After allowing the mixture to stand for half an hour, 5.5 ml of concentrated sulphuric acid are added dropwise to the solution of the formed levulinic acid-$N^1$-(5-nitro-2-furoyl)-$N^1$-(p-methoxyphenyl)-hydrazone, the mixture is stirred for an hour at 80°–85°C, then cooled and 100 ml of water are added. The precipitated 1-(5-nitro-2-furoyl)-2-methyl-5-methoxy-indole-3-yl acetic acid is filered by suction and washed with 100 ml of 60% acetic acid and consecutively with 100 ml of water. The crude 1-(5-nitro-2-furoyl)-2-methyl-5-methoxy-indole-3-yl acetic acid obtained is recrystallized from 220 ml of 88% tert. butanol. Yield: 21.6 g. (60.6%), m.p. 178°–180°C.

EXAMPLE 7

25.8 G. (0.1-mole) of sodium p-methoxyphenyl-hydrazine-sulphonate monohydrate are dissolved in a mixture of 112 ml of water and 48 ml of tert. butanol, then 17.4 g. (0.1 mole) of 5-nitro-furan-2-carboxylic acid chloride are poured into the solution, and the mixture is stirred for an hour at room temperature and consecutively for another hour on a water-bath of 70°–80°C. Subsequently, without isolating the product, 17 ml of levulinic acid and 4.5 ml of concentrated sulphuric acid are added dropwise, the mixture is stirred at 80°–85°C for an hour, cooled and 80 ml of water are added. The precipitated 1-(5-nitro-2-furoyl)-2-methyl-5-methoxy-indole-3-yl acetic acid is filtered by suction, and washed consecutively with 80 ml of 60% acetic acid and 100 ml of water. The crude product is recrystallized from 170 ml of 88% tert. butanol, clarified with 5% of active carbon "Norit", recrystallized on cooling, filtered by suction, washed with 20 ml of 88% tert. butanol, and dried to afford 17.7 g. of 1-(5-nitro-2-furoyl)-2-methyl-5-methoxy-indole-3-yl acetic acid. Yield 73.5%, m.p. 178°–180°C.

EXAMPLE 8

25.8 g (0.1 mole) of sodium p-methoxyphenylhydrazine sulphonate monohydrate are dissolved in a mixture of 112 ml of water and 48 ml of tert. butanol, and 20 g (0.11 mole) of 2-chlorothiazole-4-carboxylic acid chloride added. The reaction mixture is stirred at room temperature for an hour and at 70°C for another hour. Then, without isolating the product, 43.5 ml of levulinic acid and 5 ml of concentrated sulphuric acid are added, and the mixture is stirred at 80°C for 4 hours. On diluting the reaction mixture with water, the precipitated product is filtered by suction and recrystallized from tert. butanol, affording 23 g of 1-(2-chloro-thiazole-4-yl-carboxylic)-2-methyl-5-methoxy-indole-3-yl acetic acid. Yield: 65%, m.p. 158°–160°C.

The effect of the following compounds:
1. 1-(2-chloro-4-thiazolyl-carbonyl)-2-methyl-5-methoxy-indole-3-yl acetic acid;
2. 1-(2-bromo-4-thiazolyl-carbonyl)-2-methyl-5-methoxy-indole-3-yl acetic acid; and
3. 1-(5-nitro-2-furoyl)-2-methyl-5-methoxy-indole-3-yl-acetic acid was tried on plants. The seeds of the various plants were soaked in aqueous solutions of these compounds at the stated concentration and then the stimulating effect on the seedlings was compared (by weighing foliage and roots) to the control group whose seeds had not been soaked after 8, 12, and 18 days. The average values of the results of the stimulative effects (improvement over control) are given in the table below:

| Compound | 1 | | | 2 | | |
|---|---|---|---|---|---|---|
| | Concentration % | Stimulative effect % | | Concentration | Stimulative effect % | |
| | | roots | foliage | | roots | foliage |
| Cucumber | $10^{-8}$ | 110 | 44 | | | |
| Sugar-beet | $10^{-6}$ | 57 | 5 | $10^{-5}$ | 20–50 | 40 |
| Parsley | $10^{-5}$ | 20–40 | 25 | $10^{-5}$ | 20–60 | 35 |

| Compound | 3 | | |
|---|---|---|---|
| | Concentration % | Stimulative effect % | |
| | | roots | foliage |
| Corn | $10^{-11}$ | 30 | 32 |

-continued

| | | | |
|---|---|---|---|
| Cucumber | $10^{-7}$ | 38 | 69 |
| Peas | $10^{-15}$ | 82 | — |
| Sugar-beet | $10^{-6}$ | 85 | 83 |
| Parsley | $10^{-6}$ | 54 | 20 |

We claim:
1. A process for promoting plant growth comprising applying to the plant site after seeding an effective amount of a compound of the formula

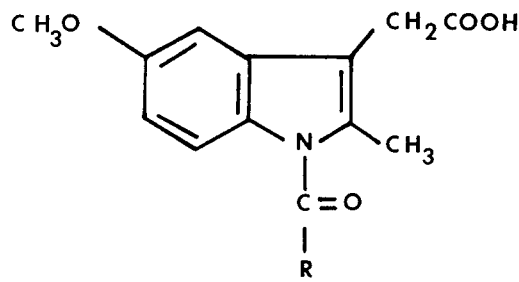

or a salt thereof wherein R is selected from the group wich consists of:
2-furyl,
5-nitro-2-furyl,
2-bromothiazol-4-yl, and
2-chlorothiazol-4-yl.

2. The process defined in claim 1 wherein said compound is 1-(5-nitro-2-furoyl)-2-methyl-5-methoxy-indole-3yl acetic acid.

3. The process defined in claim 1 wherein said compound is 1-(2-furoyl)-2-methyl-5-methoxy-indole-3-yl-acetic acid.

4. The process defined in claim 1 wherein said compound is 1-(2-bromo-thiazol-4-yl-carbonyl)-2-methyl-5-methoxy-indole-3-yl-acetic acid.

5. The process defined in claim 1 wherein said compound is 1-(2-chloro-thiazol-4-yl-carbonyl)-2-methyl-5-methoxy-indole-3-yl-acetic acid.

6. The method defined in claim 1 wherein the seed is treated with a concentration of $10^{-3}$ to $10^{-20}$ of the compound in aqueous solution.

* * * * *